(12) United States Patent
Chartoff et al.

(10) Patent No.: US 6,380,340 B1
(45) Date of Patent: Apr. 30, 2002

(54) RIGID ROD MONOMERS AND POLYMERS FOR USE IN RAPID PROTOTYPING, COMPOSITES, AND ADHESIVES

(75) Inventors: Richard P. Chartoff, Cincinnati, OH (US); Jayprakash C. Bhatt, Waltham, MA (US); Tat H. Tong, Dayton, OH (US)

(73) Assignee: University of Dayton, Dayton, OH (US)

( * ) Notice: Subject to any disclaimer, the term of this patent is extended or adjusted under 35 U.S.C. 154(b) by 0 days.

(21) Appl. No.: 09/688,998

(22) Filed: Oct. 16, 2000

Related U.S. Application Data

(62) Division of application No. 09/266,231, filed on Mar. 10, 1999.
(60) Provisional application No. 60/077,467, filed on Mar. 10, 1998.

(51) Int. Cl.[7] .......................... C08F 120/10; C08G 59/00
(52) U.S. Cl. .......................... 526/285; 528/361; 528/425
(58) Field of Search .......................... 526/285; 528/361, 528/425

(56) References Cited

U.S. PATENT DOCUMENTS 6,117,385 A * 9/2000 Chartoff ..................... 264/401

OTHER PUBLICATIONS

Schultz, J. W. et al., J. Polym. Sci., Part B: Polym. Phys. (1999). 37(11), 1183–1190.

* cited by examiner

*Primary Examiner*—Christopher Henderson
(74) *Attorney, Agent, or Firm*—Killworth, Gottman, Hagan & Schaeff, L.L.P.

(57) ABSTRACT

Rigid-rod monomers and polymers are provided for use in applications such as rapid prototyping, composites and adhesives. The monomers can be photocured through the end groups and then thermally post cured through the acetylene groups. The result is a highly crosslinked polymer having an effective glass transition temperature well above 200° C.

5 Claims, 2 Drawing Sheets

RIGID ROD MONOMERS AND POLYMERS FOR USE IN RAPID PROTOTYPING, COMPOSITES, AND ADHESIVES

CROSS REFERENCE TO RELATED APPLICATIONS

This application is a division of U.S. patent application Ser. No. 09/266,231, filed Mar. 10, 1999.

This application claims the benefit of U.S. provisional application Ser. No. 60/077,467 filed Mar. 10, 1998. Reference is also made to related U.S. application Ser. No. 09/128,078 filed Aug. 3, 1998 U.S. Pat. No. 6,117,385 entitled METHOD AND APPARATUS FOR STEREOLITHOGRAPHY.

GOVERNMENT RIGHTS

The Government has rights in this invention pursuant to Contract No. DMR-9420357 awarded by the National Science Foundation.

BACKGROUND OF THE INVENTION

The present invention relates to rigid-rod monomers and polymers for use in applications such as rapid prototyping, composites and adhesives.

In recent years, monomers have been developed for use as building materials in rapid prototyping by stereolithography and other processes as well as for use in polymer composites and adhesives. Such monomers may be used in the liquid crystal phase, which makes it possible to create layered structures with anisotropic mechanical properties by varying molecular orientation during the process of forming the polymer. However, current stereolithography methods are performed at ambient temperatures, while it is desirable for the monomers to be used in applications which require elevated temperatures, and the upper-use temperature of the cured resins needs to approach or exceed 200° C. as disclosed in related copending U.S. application Ser. No. 09/128,078, the disclosure of which is hereby incorporated by reference.

Accordingly, there is still a need in the art for the development of liquid crystalline monomers for use in rapid prototyping, composite and adhesive applications and composite applications which form highly crosslinked polymers having high glass transition temperatures.

SUMMARY OF THE INVENTION

The present invention meets those needs by providing diacrylate monomers of two types, i.e. those as shown in formula I below and those as shown in formula II below. The monomers can be photocured through the end groups and then thermally post cured through the acetylene groups. The result is a highly crosslinked polymer having an effective glass transition temperature well above 200° C.

The structural formulas for Monomer I and Monomer II are as follows:

Monomer I

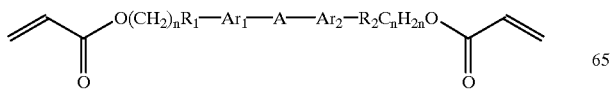

where A is C≡C

 

C(CH$_3$)=CH CH=N N=N CH=CH CO$_2$ or none, where Ar$_1$, Ar$_2$=

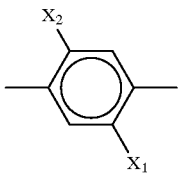 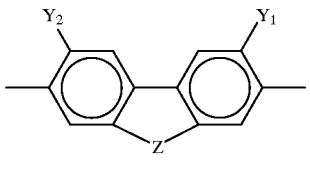

where X$_1$, X$_2$=H, F, CH$_3$, OCH$_3$, Cl, NO$_2$ or NH$_2$, where Y$_1$, Y$_2$=H, F, CH$_3$, OCH$_3$, Cl, NO$_2$ or NH$_2$, where Z=CH$_2$, NH, O, S or SO$_2$, where R$_1$ is none, O, S or C≡C, where R$_2$ is none, O, S or C≡C, and where n is 0–20.

Monomer II

where Ar is:

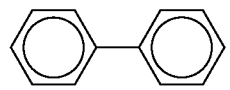

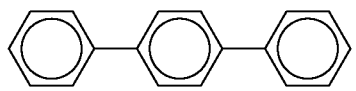

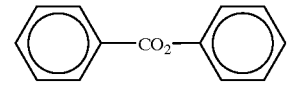

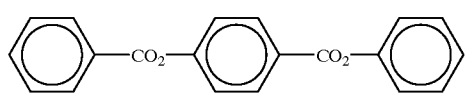

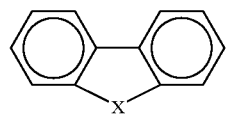

where X=CH$_2$, NH, O, S or SO$_2$, where R is acrylate, glycidyl or epoxy, and where n is 0–20.

Included within the preferred species of Monomer I are those having the following formulas:

Monomer IA

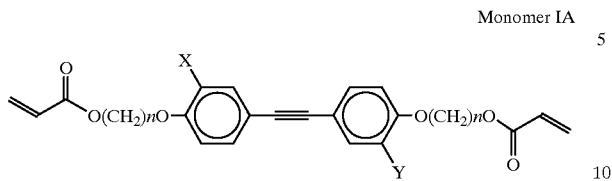

where n=3 or 6 and where in
Monomer IA1 X=Y=H,
Monomer IA2 X=Y=F,
Monomer IA3 X=F, Y=H.

Monomer IB

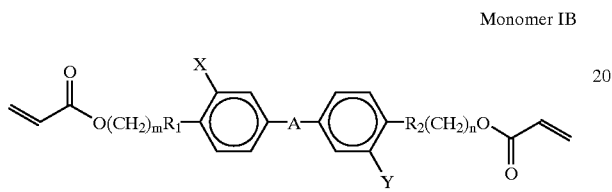

where A is:

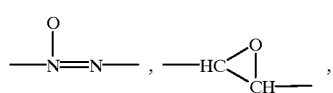

$CH=CH-$, $-C(CH_3)=CH-$, $-CO_2-$, $-CH=N=$, $-N=N-$, and

X=H, F, $CH_3$, $OCH_3$, Cl,

Y=H, F, $CH_3$, $OCH_3$, Cl, m=0–20, n=0–20, $R_1$=none, O, S, and $R_2$=none, O, S.

Included within the preferred species of Monomer II are those having the following formula:

Monomer IIA

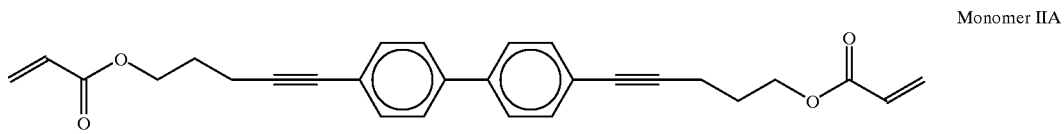

Monomer IIB

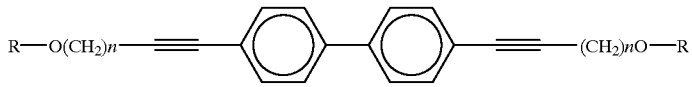

Monomer IIC

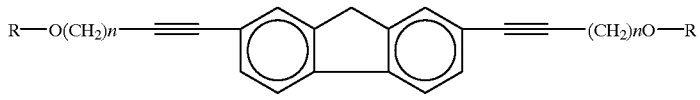

Monomer IID

Monomer IIE

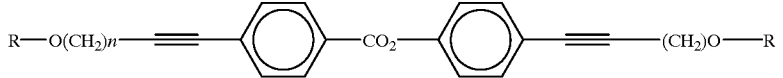

where R in IIB–IIE is acrylate, glycidyl or epoxy.

Accordingly, it is a feature of the present invention to provide novel rigid rod monomers and polymers for use in rapid prototyping, composites and adhesives, and more particularly to provide two types of diacrylate monomers and resulting polymers for such uses. This, and other features and advantages of the present invention will become apparent from the following detailed description and the appended claims.

DETAILED DESCRIPTION OF THE PREFERRED EMBODIMENT

Figure 1:
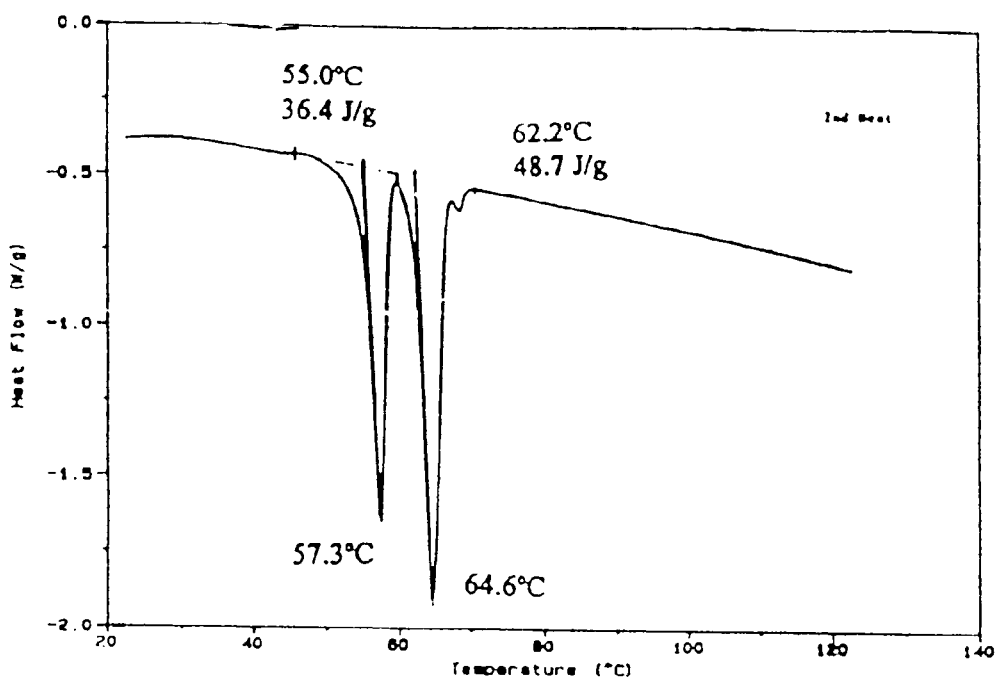
FIG. 1 is a Differential Scanning Colorimeter of Monomer IA2, where n is 3, at 5° C./min.

The present invention provides an advantage in that the synthesis procedure for the monomers is less complicated than previous methods, making the process less expensive to implement. In addition to stereolithography, the monomers may be useful in applications for adhesives, composite matrix resins, and optical devices.

Synthesis of Monomer IA is shown in Scheme I below. First, the hydroxy group of the phenol is protected as a tetrohydropyranol ether. The next step is a three step one pot reaction to convert the protected phenol 4 to the diphenylacetylene compound 5 by reaction with 2-methyl-3-butyn-2-ol in the presence of dichlorobis(triphenylphosphine) palladium (II) as catalyst. Reaction of the diphenylacetylene compound 5 with HCl gives the diphenol 6 which is then converted to the dialcohol 7 by reaction with 3-bromo-1-propanol or 6-bromo1-hexanol. The dialcohol 7 is then reacted with acryloyl chloride to obtain the desired monomers IA 1, IA2, and IA3.

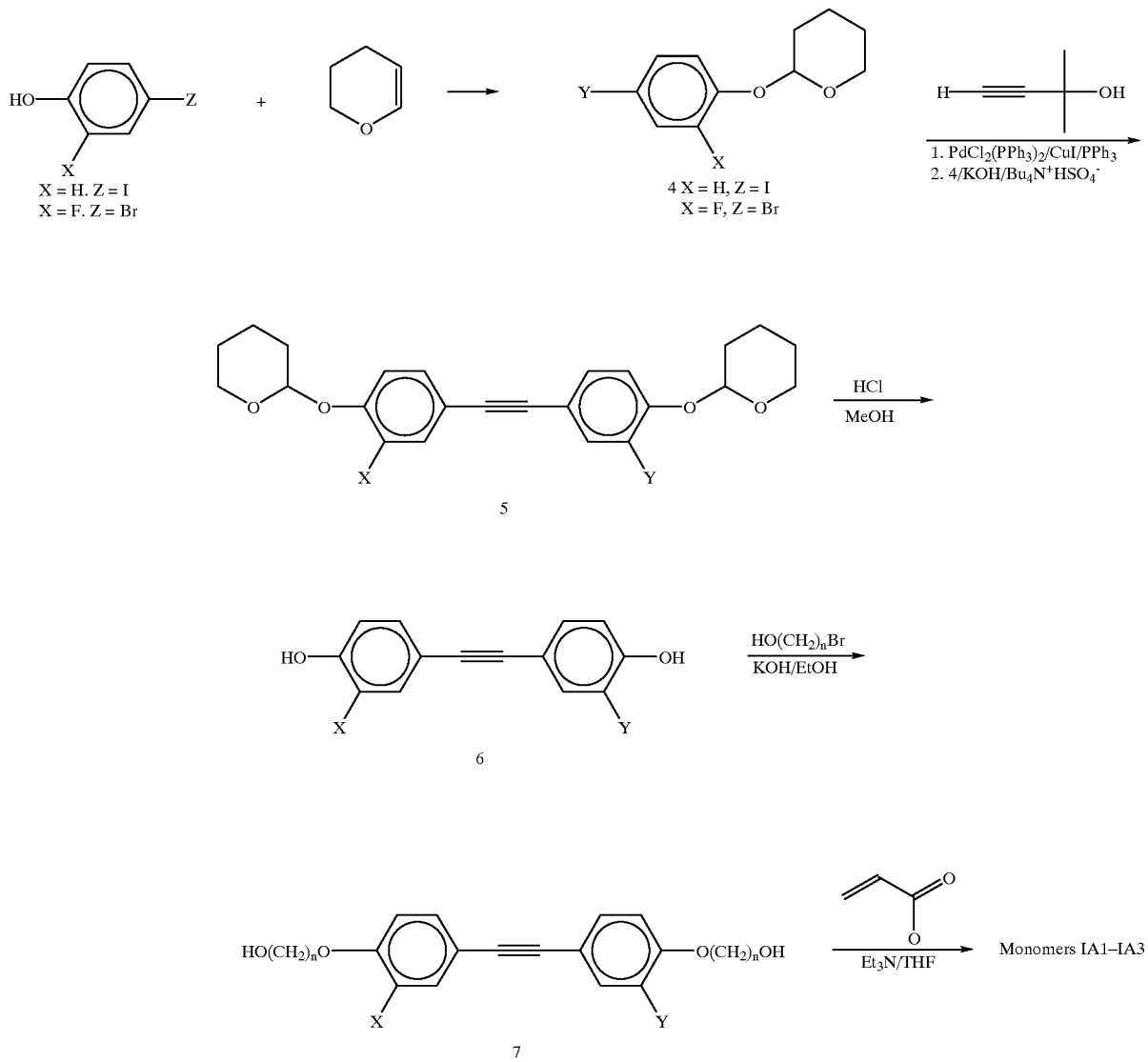

Scheme I

Phase Behavior of Monomers IA1–IA3

The phase transition temperatures for Monomers IA1 to IA3 was done by Differential Scanning Calorimetry. The phases were identified using hot stage polarizing microscopy. The data is presented in Table 1 below.

TABLE 1

| Compound | Transition Temperatures ° C. | | |
|---|---|---|---|
| IA 1a | heat | K→I | 88.0 |
| X = Y = H, n = 3 | cool | I→K | 67.2 |
| IA 1b | heat | K→I | 70.1–70.6 |
| | cool | I→S | 69.8–68.4 |
| | | S→K | 57.4 | diphenyl acetylene, the required intermediate would be compound 9.

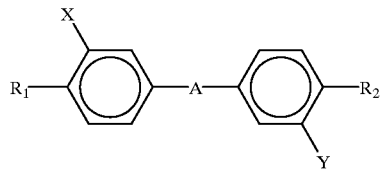

Synthesis of Monomer IIA is shown in Scheme II below.

Scheme II

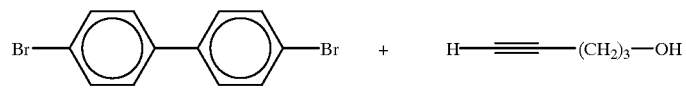

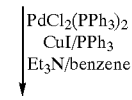

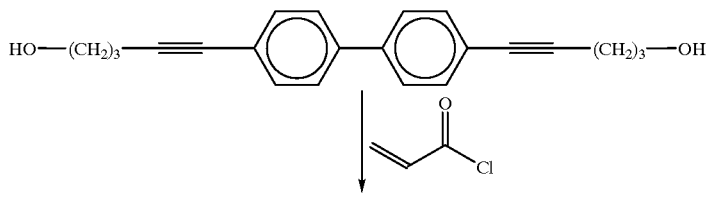

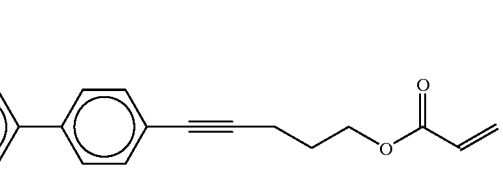

TABLE 1-continued

| Compound | Transition Temperatures ° C. | | |
|---|---|---|---|
| IA 2a | heat | K→I | 68.3 |
| X = Y = F, n = 3 | cool | I→K$_1$ + K$_2$ | 44.0 |
| | heat | K$_1$→I | 57.4 |
| | | K$_2$→I | 64.6 |
| IA 2b | heat | K→I | 69.5 |
| X = F, n = 6 | cool | I→K | 48.0 |
| IA 3a | heat | K→I | 65.5–66.5 |
| X = H, Y = F, n = 3 | cool | I→S | 50.6 |
| | | S→K | 48.6 |
| IA 3c | heat | K→I | 49.6 |
| X = H, Y = F, n = 6 | cool | I→K | 40.1 |
| | | S→K | 39.2 |

Synthesis of Monomer IB can be achieved by simple variations in Scheme I. Instead of synthesis of dihydroxy- Synthesis of the epoxy terminated monomers can be carried out following the procedure of Carfagna et al., "Liquid Crystalline Epoxy Resins: A Glycidyl Terminated Benzaldehyde Azine Cured in the Nematic Phase," *Macromol. Chem. Phys.,* 195, 279 (1994). The process consists of converting a dihydroxy compound to its sodium salt under anhydrous conditions followed by treatment with epichlorohydrin. Anhydrous conditions are required to prevent hydrolysis of the ester linkages which would occur if the typical production methods for epoxy resin preparation were employed. The diglycidyl compound is the product of the reaction. The process is illustrated below with preparation of the epoxy equivalent of diacrylate Monomer IID. The preparation is a one pot reaction which occurs in good yields even though it consists of two steps.

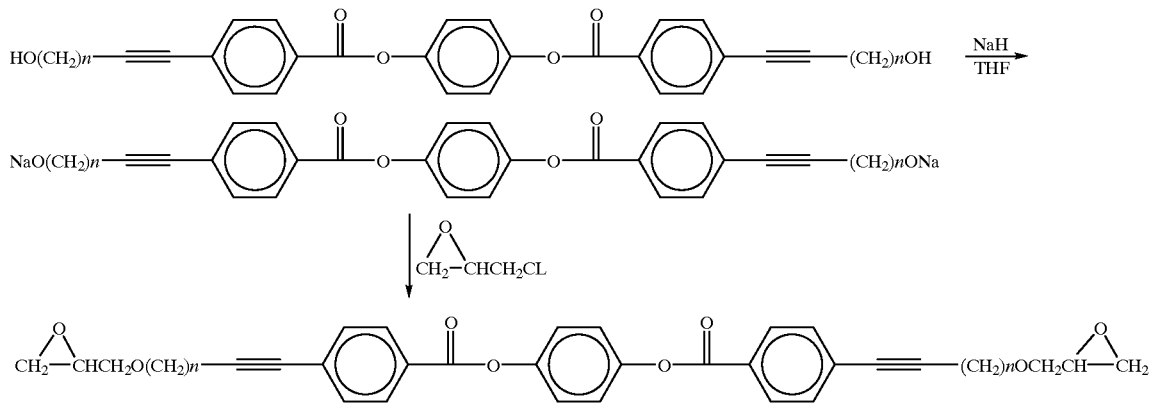

In order that the invention may be more readily understood, reference is made to the following examples, which are intended to be illustrative of the invention, but are not intended to be limiting in scope.

EXAMPLE 1

Monomer IA2, where n is 3, was synthesized using Scheme I. All chemicals were obtained from Aldrich Chemical Co. Newly synthesized compounds were thoroughly purified and their purity checked by HPLC with a C-18 column and methanol as eluting solvent. Samples of photopolymerization were prepared with 1.5% Irgacure 369 [2-benzyl-2-N,N-dimethylamino-1-(4-morpholinophenyl)-1-butanone, Ciba Additives] as a photoinitiator.

Samples were analyzed using a TA Instruments 2910 differential scanning calorimeter (DSC) and a 2940 thermno-mechanical analyzer (TMA). Those samples prepared for thermomechanical analysis were held at 80° C. and irradiated using a short-arc mercury lamp (Ultracure 100, EFOS Inc.) held approximately 2 cm above the sample surface. Curing studies were conducted using Perkin-Elmer DSC-7 differential scanning calorimeter equipped with a Perkin-Elmer DPA-7 photocalorimetry accessory. Finally, UV-Vis spectra of the neat monomer were obtained with a Hewlett Packard HP8452 Diode Array UV-Vis Spectrophotometer.

For the sake of simplicity, synthesis of compounds where X=Y=F, where n is 3, is described. This is Monomer IA2 above. The synthesis of compounds where X=Y=H, where n is also 3, was done by a similar procedure. This is Monomer IA1. Melting points of all the compounds are reported.

Synthesis

Preparation of 2-(4-bromo-2-fluorophenyl) tetrahydropyranol ether: p-Toluene sulfonic acid (0.40 g) was added to an ice-cooled solution of 4-Bromo-2-fluoro phenol (205.38, 1.075 mol) in dihydro-2H-pyran (452.23 g, 5.376 moles). The ice bath was removed after 30 min. and the mixture was stirred for two hours and then diluted with methylene chloride (500 ml). The methylene chloride solution was extracted with 10% aqueous KOH solution (3×500 ml), rinsed with water (3×500 ml), dried over MgSO$_4$, filtered and rotavaped. The crude product was further dried overnight over a vacuum pump and then vacuum distilled. The first distillation fraction was unreacted phenol, (52.0 g) followed by a fraction of the protected phenol (212.29 g, 71.8%). The purified product was frozen in dry ice/acetone bath and then allowed to sit in the refrigerator over 2–3 days to obtain the Monomer IA2 intermediate as clear needle shaped crystals, mp=25–27° C., mp of the Monomer IA1 intermediate=62–63° C., TLC (1:1 CH$_2$Cl$_2$/hexane), R$_f$=0.42.

Preparation of 4,4'-Bis(2-dihydropyranyloxy)-3-3'-difluorodiphenylacetylene: A solution of 2-methyl-3-butyn-2-ol (2.80g, 34.0 mmol) and triethyl amine (6.17 g, 61.0 mmol) in degassed benzene was added to a mixture of cuprous iodide (1.00 g, 5.3 mmol), triphenylphosphine (1.89 g, 7.2 mmol), bis(triphenylphosphine) Palladium (II) chloride (0.98 g, 1.4 mmol) and protected phenol (8.53 g, 31.0 mmol). The mixture was stirred and refluxed under nitrogen atmosphere for 12–16 hours and then cooled to room temperature. A solution of protected phenol (8.80 g, 32.0 mmol) in degassed benzene/tetrahydrofuran (20 ml; 9:1) was added followed by addition of finely ground mixture of KOH (8.42 g, 150.0 mmol) and tetrabutylammonium hydrogen sulfate (0.88 g, 2.60 mmol). The reaction mixture was further refluxed for 24 hr., then cooled to room temperature. A saturated aqueous solution of ammonium chloride (400 ml) was added and stirred for 1–2 hr. Aqueous and organic phases were separated, the aqueous solution was extracted with benzene (5×100 ml) and the combined organic phase was rinsed with water (2×400 ml). The benzene solution was dried over MgSO$_4$, rotavaped and the crude product was purified by chromatography on silica gel using 5–10% THF/hexane as eluting solvent. The chromatographed material was stirred with hexane (150 ml) and filtered to obtain pure Monomer IA2 intermediate (5.28 g, 41.1%). TLC (1:1 CH$_2$Cl$_2$/hexane), R$_f$=0.22, mp=108–110° C., mp of the Monomer IA1 intermediate=140–144° C.

Preparation of 4,4'-dihydroxy-3,3'-difluorodiphenylacetylene: Concentrated HCl (1.49 ml of 12.1 M, 18.1 mmol) was added to a stirred mixture of protected phenol (2.50 g, 6.03 mmol) and methanol (135 ml). The material was completely dissolved in 1.0 hr. The reaction was stirred at room temperature for 4 hr., after which NaHCO$_3$ (3.04 g, 36.2 mmol) was added and stirring continued for another hour. The methanol solution was rotavaped, the residue dried over a vacuum pump and then stirred with water (250 ml) for 1 hr. The crude product (1.52 g) was filtered, air dried and was used without further purification. TLC (10% EtOAc/CH$_2$Cl$_2$ ), R$_f$=0.35, mp=184–186° C., mp of the Monomer IA1 intermediate= 186–189° C.

Preparation of 4.4'Bis (3-hydroxypropyloxy)-3.3'-difluorodiphenylacetylene: A solution of ground KOH (0.73 g, 13.1 mmol) in ethanol (15 ml) was added in small portions to a stirred solution of 3-bromo-1-propanol (1.81 g, 13.1 mmol) and the difluoro phenol (1.46g, 5.9 mmol) in ethanol (10 ml). The mixture gradually warmed and refluxed for 4 hr after which more bromopropanol (1.60 g, 11.5 mmol) and KOH (0.25 g, 4.5 mmol) were added. The reaction was refluxed for additional 3 hr. cooled, ethanol removed on rotary evaporator and the residue further dried on vacuum pump. The dried residue was stirred with water (75 ml) for 1 hr, filtered and filtration residue washed with water and air dried. Purified compound (1.10 g, 51.2%) was obtained either by recrystallization from 2-butanone or chromatography on silica gel column using 10–30% THF/$CH_2Cl_2$ as eluting solvent. TLC (20% THF/$CH_2Cl_2$) $R_f$=0.21, mp=137–138° C., mp of the Monomer IA1 intermediate=158–160° C.

Preparation of Diacrylate Monomer IA2: A solution of acryloyl chloride (0.75g, 0.67 ml, 8.28 mmol) in freshly distilled $CH_2Cl_2$ (10 ml) was added dropwise over 1 hr to a cooled solution (ice+$NH_4Cl$ bath, −2–0° C.) of a dialcohol (1.00 g, 2.76 mmol) and $Et_3N$ (0.98 g, 135 ml, 9.66 mmol) in freshly distilled THF (20 ml). The reaction was stirred in cold for 5 hr, the ice bath was removed and stirred for another 3 hr. All the solvent was removed on a vacuum pump, the white residue was preadsorbed on silica gel from a $CH_2Cl_2$ solution and chromatographed on silica gel using 10–25% THF/hexane as eluting solvent. The purified diacrylate Monomer IA2 (0.80g, 61.54%) was obtained as a white fluffy solid by freeze drying from a benzene solution.

Results and Discussion

Differential Scanning Calorimetry and Thermal Polymerization

DSC analysis of Monomer IA2 reveals the importance of thermal history in understanding phase behavior. Upon first heating the sample, a broad crystal to isotropic melting transition reaches a maximum at 68.3 ° C. Upon cooling, the material supercools by about 25° C. to crystallize into two crystal forms at 44.0° C. As the sample is heated a second time (FIG. 1), the two crystalline forms melt to isotropic liquids at 57.4 and 64.6° C., respectively.

The DSC scan of Monomer IA1 shows a broad crystal to isotropic transition reaching a maximum at 88.0° C. Upon cooling, the material supercools by about 20° C. to crystallize sharply at 67.2° C. On heating, the material to high temperature, the acrylate begins to thermally cure at 225° C. and reaches a maximum at 255.4° C. Attempts to heat the material further to observe the acetylene cure, indicate that the Monomer IA1 begins to degrade at or below the acetylene cure temperature.

UV-Vis Spectroscopy

UV-Vis absorption spectroscopy provides important information for use in developing materials for photocuring applications. In such applications, it is necessary to select a photoinitiator that has a high absorptivity coefficient outside the range of the monomer. It is also important to consider the chemical environment when making such measurements. In methanol solution, Monomer IA2 displays four partially resolved absorption bands with maxima at 238, 260, 298 and 338 =nm and an absorption cutoff at approximately 350 nm. In contrast, the neat monomer exhibits a single broad absorption band, with several unresolved peaks. Additionally, a bathochromic shift can be observed that causes the absorption cutoff to increase to approximately 370 nm in the neat monomer. From the absorption data, it was possible to determine appropriate photoiniators, as well as irradiation wavelengths, for the monomers of interest.

Photocalorimetry

Comparison of the photocalorimetry response of Monomer IA2 with that of a commercially available acrylate resins used for stereolithography shows that the initial reaction rates of the two resins is very similar. However, the overall reaction of the commercial resin is much faster than for the material of interest. Experiments are currently underway to examine the kinetics of these reactions in order to better understand how the polymerization may be controlled.

Thermomechanical Analysis

Figure 2:
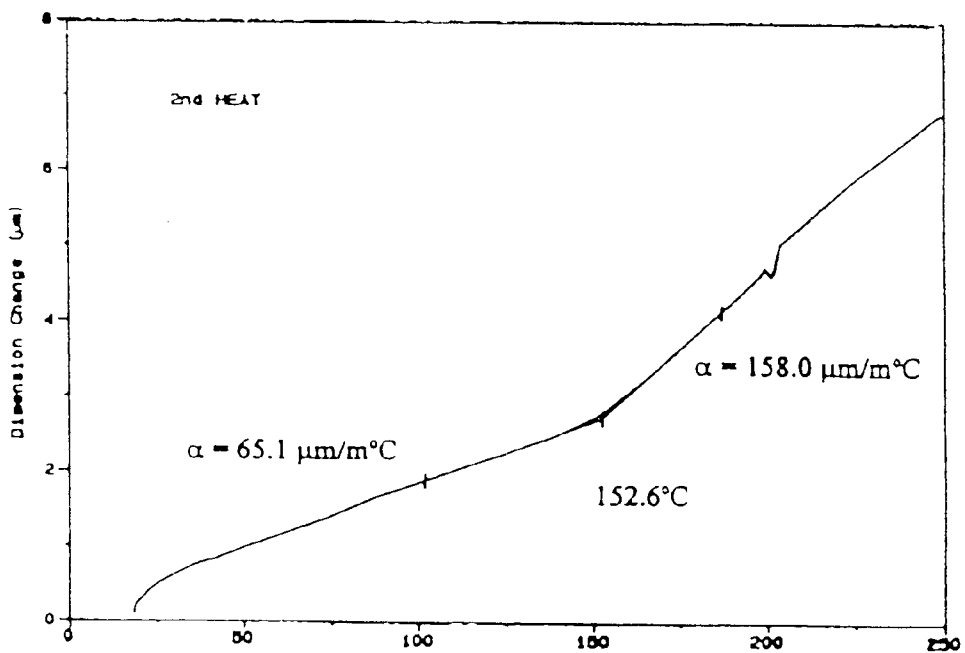
FIG. 2 is a Thermo-mechanical analysis of cured Monomer IA2, where n is 3, expansion mode; at 5° C./min.

TMA of the photopolymer prepared from Monomer IA2 indicates that the initial $T_g$ is approximately 144° C. After heating to 250° C., the sample was reheated to reveal a final $T_g$ of approximately 153° C. (FIG. 2).

Conclusion

Two new diphenyl acetylene-containing diacrylate Monomers IA2 and IA1 were synthesized. The DSC results confirm the lowering of the transition temperature by introducing lateral fluoro substituents. The photocuring conditions for the Monomer IA2 compound were optimized. The glass transition temperature of the Monomer IA2 was lower than that of the stilbene monomer reported earlier in Bhatt, J. C.; Dotrong, M. H.; Pogue, R. T.; Ullett, J. S. and Chartoff, R. P. Preprint, 37 (2), (1997). This is most likely due to the fact that the packing, density of Monomer IA2 is less than that of the Stilbene monomer.

EXAMPLE 2

Monomer IIA was synthesized using Scheme II using the following materials from the listed sources.

| Material | Source |
| --- | --- |
| 4,4'-dibromodiphenyl | IGC[a] |
| 4-pentyn-1-ol | IGC |
| dichloro(bistriphenyl-phosphine) palladium (II) | Pressure[b] |
| triphenylphosphine | Pressure |
| acryloyl chloride | Aldrich[d] |
| copper(1)iodide | Aldrich |
| triethylamine | Aldrich |
| benzene | Fisher[e] (B245-4) |
| tetrahydrofuran | Fisher (T42504) |
| sodium | Aldrich (21, 710-7) |
| hexane | Fisher (H292-200) |
| ethanol | Fisher (A962P-4) |
| silica gel | Scientific[c] |

[a]International Chemical Group of San Diego, California
[b]Pressure Chemical Company of Pittsburgh, Pennsylvania
[c]Scientific Absorbents Inc. of Atlanta, Georgia
[d]Aldrich Chemical Co. of Milwaukee, Wisconsin
[e]Fisher Scientific of Pittsburgh, Pennsylvania 4,4'-(Bis-5-hydroxy-1-pentenyl)biphenyl(BHPB)

One hundred millimoles of 4,4'-dibromobiphenyl (32.0 g) (Aldrich 98%) was dissolved in 210 ml of degassed benzene in a reaction flask equipped with a mechanical stirrer, reflux condenser and an additional funnel. Dichlorobis (triphenylphosphine)palladium (3.6 g. 0.05 mole %)

(Aldrich 98%), CuI (2.93 g, 0.15 mole %) (Aldrich 98%), triphenylphosphine (6.73 g, 0.25 mole %) (Aldrich 99%) and triethylamine (31.1 g, 300 mole %) were added in the above order. The reaction mixture was stirred at room temperature for 30 minutes. 15 ml of a solution of 4-pentyn-1-ol (38.3g, 220 mole %) (Aldrich 97%) in 20 ml benzene was added and the reaction stirred for 30 minutes at room temperature. The solution became clear. The reaction mixture was heated to reflux and the rest of the 4-pentyn-1-ol solution was added dropwise over the period of 30 minutes. The mixture was refluxed for 4 hours.

The cooled solution was diluted with 1000 ml of benzene and heated to reflux. The hot solution was filtered rapidly to remove a black residue that is mainly triethylamine hydrochloride. The filtrate was concentrated to approximately 600 ml and allowed to cool. A yellow solid weighing 17.3 g was obtained. This solid was stirred with 350 ml of water to remove any remaining water soluble materials. The solid was then recrystallized from approximately 650 ml of a mixture of 80/20 v/v ethyl alcohol/water to give 11.0 g of product. The filtrate was reduced to about half volume and a second crop of product weighing 1.8 g obtained. Yield was 39.2%.

Diacrylate ester of (BHPB)

A solution of 5.0 g of BHPB (15.7 millimole) in 60 ml of freshly distilled tetrahydrofuran (THF) distilled from sodium to remove traces of water and 6.6 ml of triethylamine (47.1 millimole) was prepared in a reaction flask fitted with a mechanical stirrer, dry nitrogen purge and pressure equalizing dropping funnel. A solution of 2.48g of acryloyl chloride (Aldrich 96%) in 30 ml freshly distilled tetrahydrofuran (see Note) was added dropwise over 60 minutes. The reaction mixture was stirred at room temperature for an additional hour. The solvent was removed on a rotary evaporator with the last traces being removed using a vacuum pump. The residue was dissolved in 40 ml of tetrahydrofuran and 40 ml hexane. This solution was added to a short silica gel column (about 10 gms of silica gel per gram of product and eluted with a solution of 1/3 tetrahydrofuran/hexane. This required about 200 ml of solvent per gram of product. This THF is reagent grade and not the purified THF used in the reaction. Removal of the solvent gave a white solid. This solid was taken up 20 ml of benzene and freeze dried to give the product weighing 3.71 g, 55.4% yield. This latter step was done to remove traces of solvent that sometimes occur in this preparation. It may not be needed in this case but was done as a precaution since this was the first time the material was prepared. Analysis by HPLC on a C18 column using methanol as the mobile phase showed only one product.

Note: The THF purification was carried out by adding sodium sand and benzophenone (about 0.1%) to THF and refluxing until a blue color was obtained. This indicates that the THF is dry. The necessary quantity was then collected and used. The same still containing the sodium sand and benzophenone can continue to be used as long as a blue color is obtained after reflux.

Figure 3:
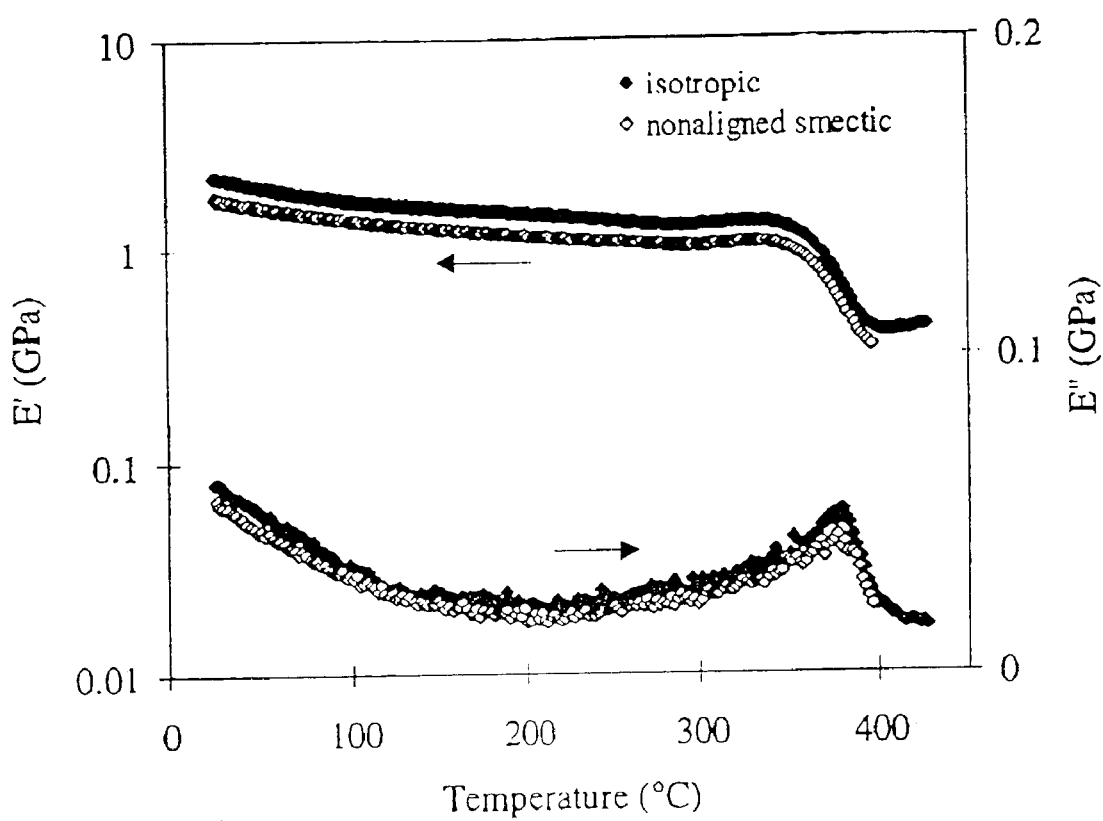
FIG. 3 is a graph illustrating the high glass transition temperature for cured Monomer IIA.

FIG. 3 shows the dynamic mechanical storage modulus and loss modulus for Monomer IIA photocured at low temperatures in both the isotropic and smectic states followed by thermal postcure.

While certain representative embodiments and details have been shown for purposes of illustrating the invention, it will be apparent to those skilled in the art that various changes in the monomers and polymers disclosed therein may be made without departing from the scope of the invention, which is defined in the appended claims.

What is claimed is:

1. A polymer produced by curing a monomer having the formula:

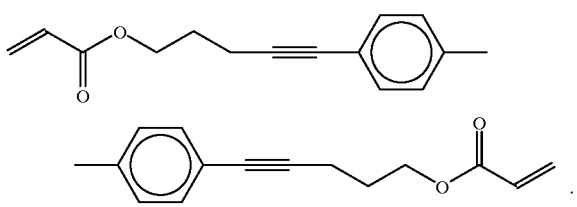

2. A polymer produced by curing a monomer having the formula:

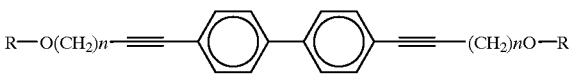

where R is glycidyl or epoxy.

3. A polymer produced by curing a monomer having the formula:

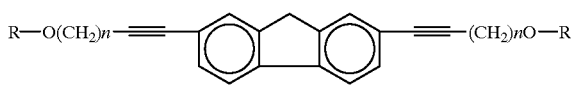

where R is glycidyl or epoxy.

4. A polymer produced by curing a monomer having the formula:

where R is glycidyl or epoxy.

5. A polymer produced by curing a monomer having the formula:

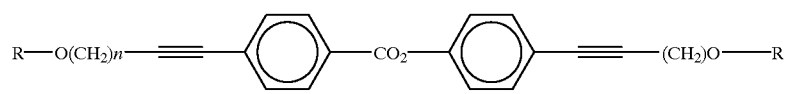

where R is glycidyl or epoxy.

* * * * *